(12) United States Patent
Narke et al.

(10) Patent No.: US 11,257,572 B1
(45) Date of Patent: Feb. 22, 2022

(54) REMOTE MEDICAL TREATMENT APPLICATION AND OPERATING PLATFORM

(71) Applicant: West Corporation, Omaha, NE (US)

(72) Inventors: Fonda J. Narke, Papillion, NE (US); Hendryanto Rilantono, Omaha, NE (US)

(73) Assignee: INTRADO CORPORATION, Omaha, NE (US)

(*) Notice: Subject to any disclaimer, the term of this patent is extended or adjusted under 35 U.S.C. 154(b) by 273 days.

(21) Appl. No.: 15/084,990

(22) Filed: Mar. 30, 2016

(51) Int. Cl.
 *G16H 10/60* (2018.01)
 *G06F 19/00* (2018.01)
 *G16H 50/30* (2018.01)

(52) U.S. Cl.
 CPC .......... *G16H 10/60* (2018.01); *G06F 19/324* (2013.01); *G06F 19/3456* (2013.01); *G16H 50/30* (2018.01)

(58) Field of Classification Search
 CPC ...... G16H 10/60; G16H 50/30; G06F 19/322; G06F 19/3456
 See application file for complete search history.

(56) References Cited

U.S. PATENT DOCUMENTS

| 2005/0251415 | A1 | 11/2005 | Pak |
| 2005/0256746 | A1 | 11/2005 | Zaleski |
| 2007/0150314 | A1 | 6/2007 | Abraham-Fuchs et al. |
| 2007/0185732 | A1 | 8/2007 | Hicks et al. |
| 2008/0133290 | A1* | 6/2008 | Siegrist ............... G06Q 10/00 705/2 |
| 2010/0222649 | A1 | 9/2010 | Schoenberg |
| 2011/0301982 | A1* | 12/2011 | Green, Jr. ............ G06Q 10/06 705/3 |
| 2012/0116180 | A1 | 5/2012 | Rothman et al. |
| 2014/0058755 | A1 | 2/2014 | Macoviak et al. |
| 2014/0276552 | A1* | 9/2014 | Nguyen, Jr. .......... G16H 20/17 604/503 |
| 2015/0046189 | A1 | 2/2015 | Dao |
| 2015/0052160 | A1* | 2/2015 | Hussam ............. G06F 16/2455 707/755 |
| 2016/0100097 | A1* | 4/2016 | Chaudhry ............ H04N 9/8205 348/333.02 |
| 2018/0018429 | A1* | 1/2018 | Rice ...................... G06Q 50/22 |

* cited by examiner

*Primary Examiner* — Robert A Sorey
*Assistant Examiner* — Kimberly A. Sass

(57) ABSTRACT

A user may require medical attention based on one or more preferences, present insurance policies, and other relevant factors. The user may also desire to participate in an audio and/or video medicine treatment option across a network. One example method may identifying an upcoming appointment time for a live medical treatment session stored in a calendar entry, creating a communication session hosted by a server, transmitting a first invitation message to a medical professional device associated with a medical professional identified in the calendar entry, transmitting a second invitation message to a user device associated with a patient identified in the calendar entry, and responsive to receiving a response message from the medical professional device, retrieving a patient profile record associated with the patient and populating a user interface of the medical professional device with patient history information stored in the patient profile record.

20 Claims, 13 Drawing Sheets

REMOTE MEDICAL TREATMENT APPLICATION AND OPERATING PLATFORM

CROSS-REFERENCE TO RELATED APPLICATION

This application is related to co-pending application Nos. PAT-264A and PAT-264C, the entire contents of which are hereby incorporated by reference.

TECHNICAL FIELD OF THE APPLICATION

This application relates to a configuration and procedure for establishing a remote telecommunications medical assistance platform, and more particularly to establishing a remote patient appointment procedure, maintaining a patient appointment schedule and providing a follow-up procedure for continued patient care.

BACKGROUND OF THE APPLICATION

Conventionally, when a user desires to seek patient care, the user is inclined to call a doctor's office to speak with a staff member and to create an appointment for a live in-person session with a physician. FIG. 1 illustrates such a conventional prior art scenario 100 where a user 102 can access a communication device 110, such as a smartphone, cell phone, landline phone or even a computing device, such as a computer or laptop and contact a specific physician of interest directly by dialing the office of that physician, such as a general practice physician, a specialist physician etc. The communication may include a direct connection to the physician office over a communication network 130, or to a website, a phone, email, etc., associated with the physician's office 120. The physician 122 or the assistant to the medical treatment center may update a computer record 124 to reflect the user's upcoming appointment via an action taken by at the location of the physician's office 120.

In general, all the decisions to link the user with the physician are either initiated by that particular physician, or in the more likely scenario, via the medical patient 102 attempting to locate the physician office and setup the physician appointment by a direct dial or communication effort. The patient can be burdened by the effort of establishing such an appointment. Also, the patient may be contacting a physician that is not his or her ideal match for medical treatment for any number of reasons. In summary, the selection and setup of the appointment is performed blindly without any assistance or third party efforts. As the request is received the appointment is likely setup without any specific information. The result is a quality of care that may or may not be suitable for that particular patient. Additionally, the type of appointment almost always requires the patient to travel to the physician office and to follow-up during his or her own time to reach any conclusions to the original appointment. Options with regard to the appointments, knowledge of the purpose for the appointment, and other sources of information may all be outcome determinative variables which should be identified and processed upfront prior to any appointment.

SUMMARY OF THE APPLICATION

Example embodiments of the present application provide a method which includes at least one of receiving a request for medical assistance from a user device, retrieving a user profile comprising user information linked to the user device, identifying at least one medical condition associated with the user information, retrieving a plurality of medical professional profiles associated with the at least one medical condition, filtering the plurality of medical professional profiles via a plurality of user preferences stored in the user information, creating a link to a list of the medical professional profiles and transmitting the link to the user device, and creating an appointment for a live medical session conference between the user device and a medical professional device associated with at least one of the plurality of medical professional profiles.

Another example embodiment may provide an apparatus which includes a receiver configured to receive a request for medical assistance from a user device, and a processor configure to perform at least one of retrieve a user profile comprising user information linked to the user device, identify at least one medical condition associated with the user information, retrieve a plurality of medical professional profiles associated with the at least one medical condition, filter the plurality of medical professional profiles via a plurality of user preferences stored in the user information, create a link to a list of the medical professional profiles, and a transmitter configured to transmit the link to the user device, and the processor may be further configured to create an appointment for a live medical session conference between the user device and a medical professional device associated with at least one of the plurality of medical professional profiles.

Yet another example embodiment may include a non-transitory computer readable storage medium configured to store instructions that when executed causes a processor to perform at least one of receiving a request for medical assistance from a user device, retrieving a user profile comprising user information linked to the user device, identifying at least one medical condition associated with the user information, retrieving a plurality of medical professional profiles associated with the at least one medical condition, filtering the plurality of medical professional profiles via a plurality of user preferences stored in the user information, creating a link to a list of the medical professional profiles and transmitting the link to the user device, and creating an appointment for a live medical session conference between the user device and a medical professional device associated with at least one of the plurality of medical professional profiles.

Still yet another example embodiment may include a method that provides at least one of identifying an upcoming appointment time for a live medical treatment session stored in a calendar entry, creating a communication session hosted by a server, transmitting a first invitation message to a medical professional device associated with a medical professional identified in the calendar entry, transmitting a second invitation message to a user device associated with a patient identified in the calendar entry, and responsive to receiving a response message from the medical professional device, retrieving a patient profile record associated with the patient and populating a user interface of the medical professional device with patient history information stored in the patient profile record.

Still yet a further embodiment may include an apparatus with a processor configured to perform at least one of identify an upcoming appointment time for a live medical treatment session stored in a calendar entry, create a communication session hosted by a server a transmitting configured to transmit a first invitation message to a medical professional device associated with a medical professional identified in the calendar entry, a transmitter configured to transmit a second invitation message to a user device associated with a patient identified in the calendar entry, and responsive to receiving a response message from the medical professional device, the processor is configured to retrieve a patient profile record associated with the patient and populate a user interface of the medical professional device with patient history information stored in the patient profile record.

Still yet a further example embodiment may include a non-transitory computer readable storage medium configured to store instructions that when executed cause a processor to perform at least one of identifying an upcoming appointment time for a live medical treatment session stored in a calendar entry, creating a communication session hosted by a server, transmitting a first invitation message to a medical professional device associated with a medical professional identified in the calendar entry, transmitting a second invitation message to a user device associated with a patient identified in the calendar entry, and responsive to receiving a response message from the medical professional device, retrieving a patient profile record associated with the patient and populating a user interface of the medical professional device with patient history information stored in the patient profile record.

Yet still another example embodiment may include a method that includes at least one of identifying a live medical treatment session record indicating a completed live medical treatment session via a completion indicator, locating a recording for the live medical treatment session record, retrieving at least one indicator stored in the session recording, and identifying at least one action to be performed for the medical patient based on the at least one indicator.

Yet still a further example embodiment may include an apparatus with a processor configured to perform at least one of identify a live medical treatment session record indicating a completed live medical treatment session via a completion indicator, locate a recording for the live medical treatment session record, retrieve at least one indicator stored in the session recording, and identify at least one action to be performed for the medical patient based on the at least one indicator.

Yet still another further example embodiment may include a non-transitory computer readable storage medium configured to store instructions that when executed cause a processor to perform at least one of identifying a live medical treatment session record indicating a completed live medical treatment session via a completion indicator, locating a recording for the live medical treatment session record, retrieving at least one indicator stored in the session recording, and identifying at least one action to be performed for the medical patient based on the at least one indicator.

DETAILED DESCRIPTION OF THE APPLICATION

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present application, the application may be applied to many types of network data, such as, packet, frame, datagram, etc. For purposes of this application, the term "message" also includes packet, frame, datagram, and any equivalents thereof. Furthermore, while certain types of messages and signaling are depicted in exemplary embodiments of the application, the application is not limited to a certain type of message, and the application is not limited to a certain type of signaling.

Figure 1:
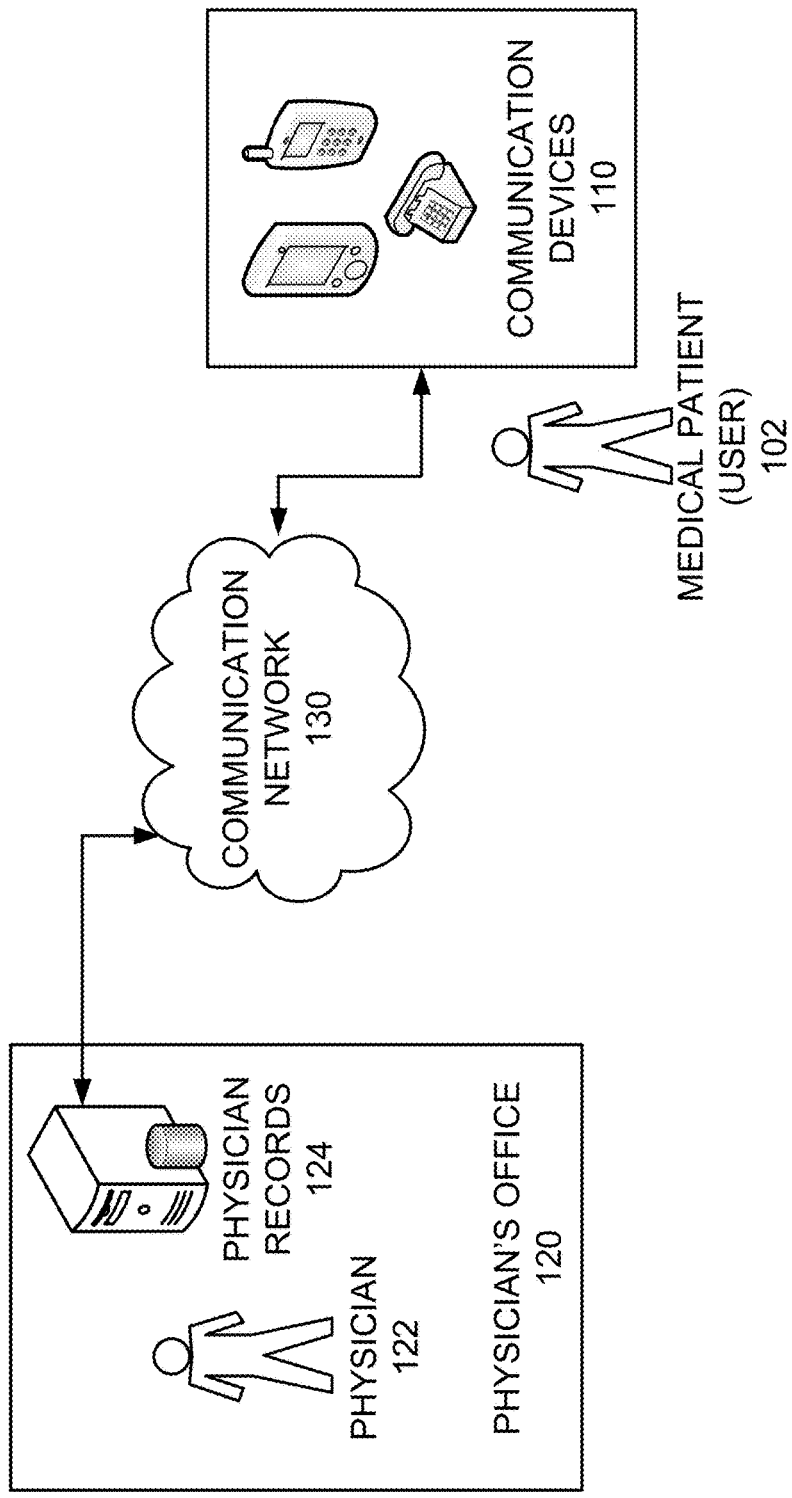
FIG. 1 illustrates an example prior art communication network and appointment setup configuration.
Figure 2:
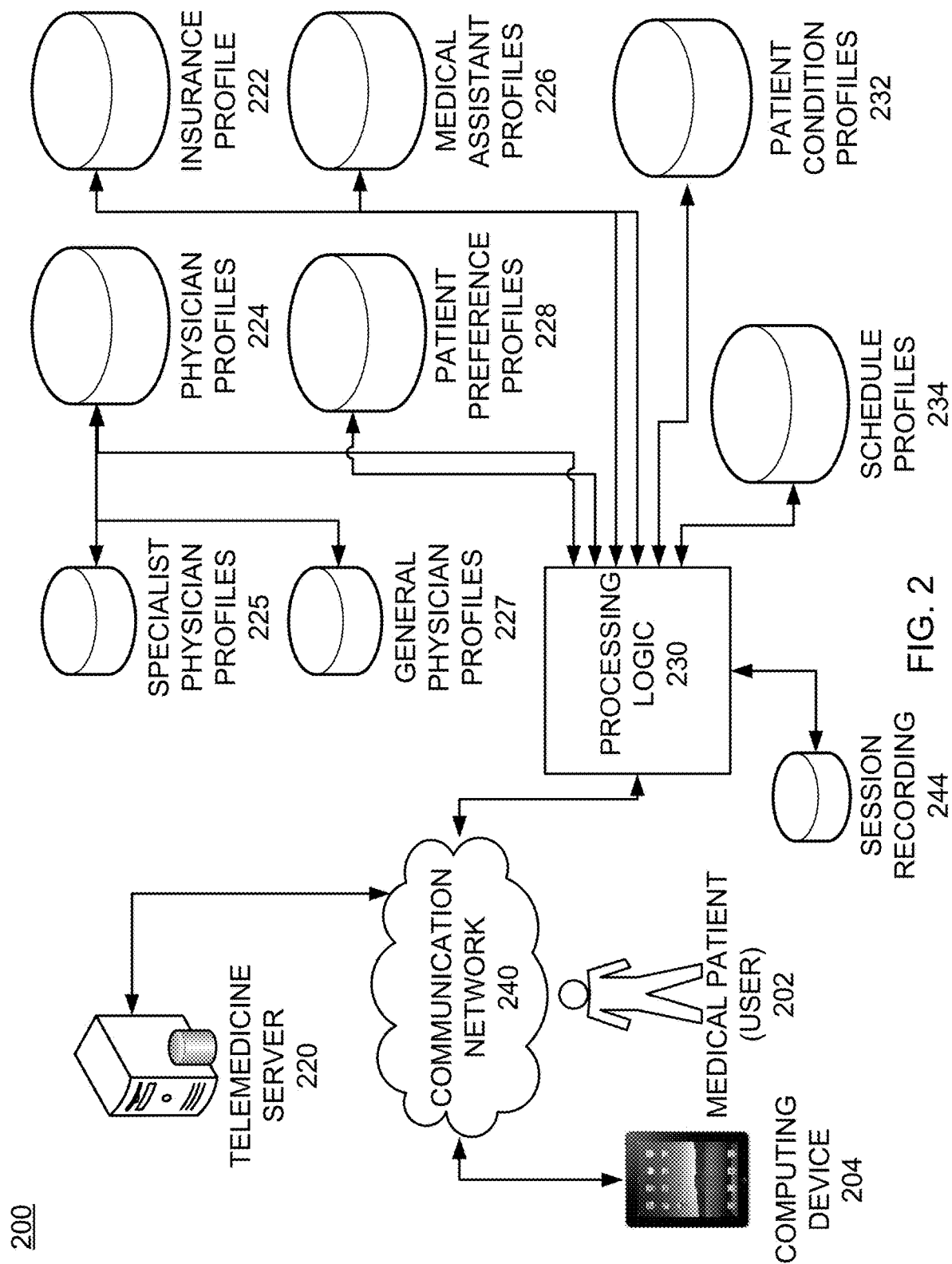
FIG. 2 illustrates an example telemedicine setup and configuration network according to example embodiments of the present application.

FIG. 2 illustrates an example telemedicine setup and configuration network according to example embodiments of the present application. Referring to FIG. 2, the network 200 includes a medical patient or user 202 accessing a computing device 204. The device may be a computer, laptop, mobile, wireless or cellular phone, a PDA, a tablet, a client a server or any device that contains a processor and/or memory, whether that processor or memory performs a function related to an embodiment of the application. The user 202 may initiate a request for a telemedicine session and/or medical assistance to a remote server 220 across a communication network 240. The user may access an account interface associated with the user's insurance or other medical assistance provider which is provided to the user for access via his or her computing device 204.

In operation, the user submitted request initiates an inquiry session that includes electronic forms, questions, etc., which the user may be required to answer prior to receiving medical care, a live telemedicine session and/or treatment from a medical professional. The request may be sent upon accessing the medical treatment application on the user's computing device 204. The request may be sent to the third party telemedicine server 220 across a network 240, such as the Internet, a private network and/or a network cloud established by the third party service provider. The request may be received and logged as part of the user's medical profile stored in the patient condition profiles 232. Processing logic 230 may retrieve and process the user's profile to update the current profile status to a 'seeking medical attention' status or an 'active' status.

Once a user profile is deemed 'active', the user profile may require an update to ensure the user's concerns are addressed properly. For example, the user device 204 may receive a number of questions relating to the user's current health and current concerns (e.g., types of pain, parts of the body experiencing pain, allergies, current prescriptions, last medical appointment, current location, current insurance, etc.). The processing logic 230 will then perform a preliminary query and provide a compiled list of preliminary treatment options. The preliminary treatment options may include a plurality of physician profiles, a plurality of treatment facilities, a plurality of alternative physician options, such as nurse practitioners, physician assistants, or other medically trained staff that could assist the user in a live computer interface session or telemedicine appointment over the user's computing device 204.

The processing logic 230 will identify the user's insurance profile 222 and the patient condition profiles 232 to ensure the results of the preliminary list of potential treatment options are filtered by those user conditions. This provides a preliminary list of potential candidates who are qualified to assist the user and which are recognized as participating in the user's insurance network. Also, a preliminary suggestion may be presented to the user based on a known user preference and/or a first objective identified by the insurance. For instance, the insurance policy profile 222 may be setup to suggest medical assistant profiles 226 which are more cost effective for common treatment options, such as cold, flu, and related symptoms often associated with a nurse practitioner or other medical assistant and which does not require a physician. If the user accepts the medical assistant option then an appointment will be automatically setup based on the available schedule policies 234 for the assistants and/or the user. The schedule policies 234 include schedules for the medical professionals and the user combined into one database structure for optimal appointment scheduling. All the known scheduling availability will be referenced so a time slot can be made available for the user 202.

In the event that the user conditions are more severe and cannot be matched to a medical assistant profile 226, then a physician will be selected based on the patient preference profile 228 and/or the patient condition profiles 232. For example, if the user is concerned about a skin condition that could be considered cancerous then a physician with experience and/or qualifications in cancer screening and/or skin screening category may be identified upfront and the medical assistant profile may be bypassed based on the elevated severity of the initial condition screening procedure performed by the processing logic 230. Severity may be elevated based on an identified condition, such as identifying the user input as "skin cancer" and parsing the term [cancer] from the user input section of the input interface of FIG. 6. Severity may be a threshold that is compared to certain medical professionals. The threshold may be a 10 point scale and the patient's condition, age, previous health conditions, etc., may all be used to calculate a function for the severity threshold. The nurse practitioners and physician assistants may be able to assist with a first threshold level T1 (less than 6.0) and not with a higher threshold level T2 (above 6.0). The patient's health history may be weighted to calculate the threshold value. For example, a cancer concern may be the highest weighted present condition (3 out of a possible 3), the patient's age 72 may be a (2.2 out of 3) and a previous cancer concern may yield a (2.4 out of a 3), and the aggregate number 7.6 may be considered a severe level requiring the patient to receive optimal care by a physician only.

Once the application is attempting to locate a physician 224, the physician profiles 224 may be referenced to identify a physician whose profile is appropriate for the initial medical conditions identified. The physician list can be referenced by both specialist profiles 225 and/or general physician profiles 227. The number of generalists is generally much more abundant and in this case the generalists may be first filtered by insurance compliance and any other user preferences.

Due to the nature of the telemedicine treatment (i.e., across computing devices), a user may have no location preference since the physician may be anywhere in the state or even the world and still provide treatment assuming the insurance credentials and licensing are upheld. However, some patients may have a preference for a physician within a certain area radius (i.e., 50 miles) in the event the user desires to follow-up with an in-person session with the physician. When selecting a general physician for a specific user health condition (i.e., potential skin cancer), the generalists may be identified and filtered via their profiles for experience in the skin examination category. Those physicians may be filtered down to a select few and the user device may receive a suggestion for any one of the select few. Also, the user may receive the physician profiles in ranked order based on the users' personal preferences. For example, if a user has five preferences including price, location, insurance compliance, years of experience, generalists before specialists, and recent experience treating a known condition, then the results may be provided to the user, for example, as 3-4 physicians listed in an order of descending compliance. The compliance order may be based on a numerical scoring function that again uses weights for the various categories of preferences and the various categories of the patient profile and history. For instance, the first physician in the list may be compatible with five or more of the user preferences and the physician name, image, and profile may be provided as part of a user interface link created and customized for the user along with the other candidates for a live telemedicine session at a later date. In this example, the user may view three other physician profiles which were ranked 2-4 to have scores of '4', '4' and '3', respectively, as complying with a corresponding number of the user preferences. When the user observes the profiles, the user may select a female or male, or a physician that speaks a language the user prefers to speak as indicated on the link of profiles, instead of the first ranked physician since other factors were readily apparent from observing the link automatically created and provided to the user. A session recording 244 may be stored in the telemedicine server 220 or a remote cloud source.

Figure 3:
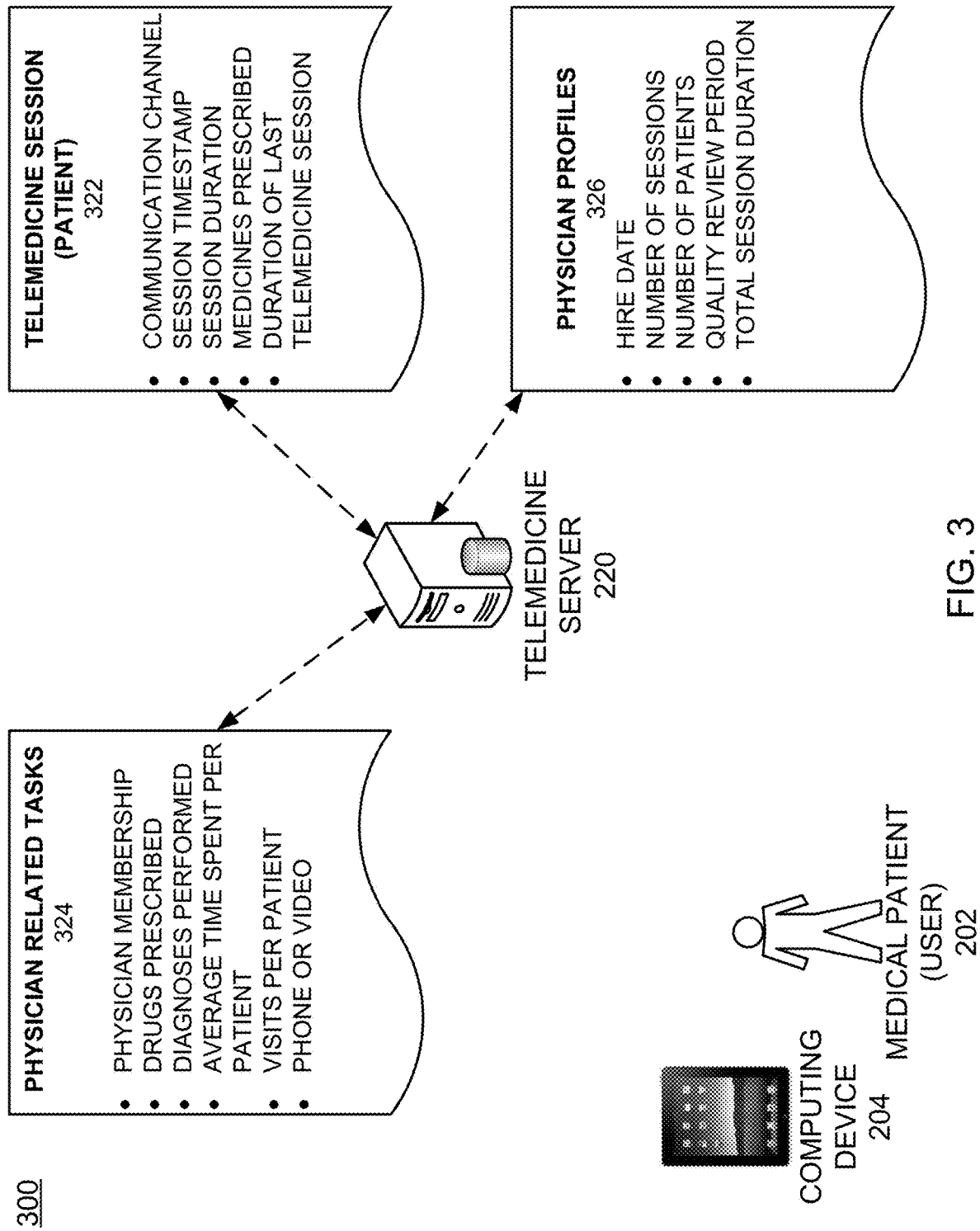
FIG. 3 illustrates a logic script execution by a telemedicine server processing patient care information for a live telemedicine session setup and execution procedure according to example embodiments of the present application.

FIG. 3 illustrates a logic script execution configuration 300 by a telemedicine server processing patient care information for a live telemedicine session setup and execution procedure according to example embodiments of the present application. Referring to FIG. 3, during a telemedicine appointment setup procedure and/or live telemedicine appointment, the telemedicine server 220 may reference information, such as the physician related tasks and other physician history information 324 including but not limited to the physician membership (i.e., credentials, insurance compliance, etc.), drugs commonly prescribed by the physician which may be stored in a database with a link to conditions treated. Also, the types of diagnoses performed by the physician(s), the average time spent per patient both in-person and via a live telemedicine conference, visits per patient for the various patients treated over the last 90 days, and/or phone or video preferences. The telemedicine session information for patients 322 may also be referenced to include, but not limited to a communication channel used (e.g., phone, Internet conferencing application, etc.), a session timestamp and duration for the patient's recent sessions, the medicines prescribed to the patient and the last telemedicine session duration. Also, the physician profiles 326 may be referenced to identify a hire date, a number of sessions conducted, a number of patients treated, a quality review period experienced by third parties providing follow-up actions and a total session duration for previous and current sessions. Such information can provide useful analyses when providing the computing device 204 with suggestions and links to resources related to creating a new telemedicine session.

Figure 4:
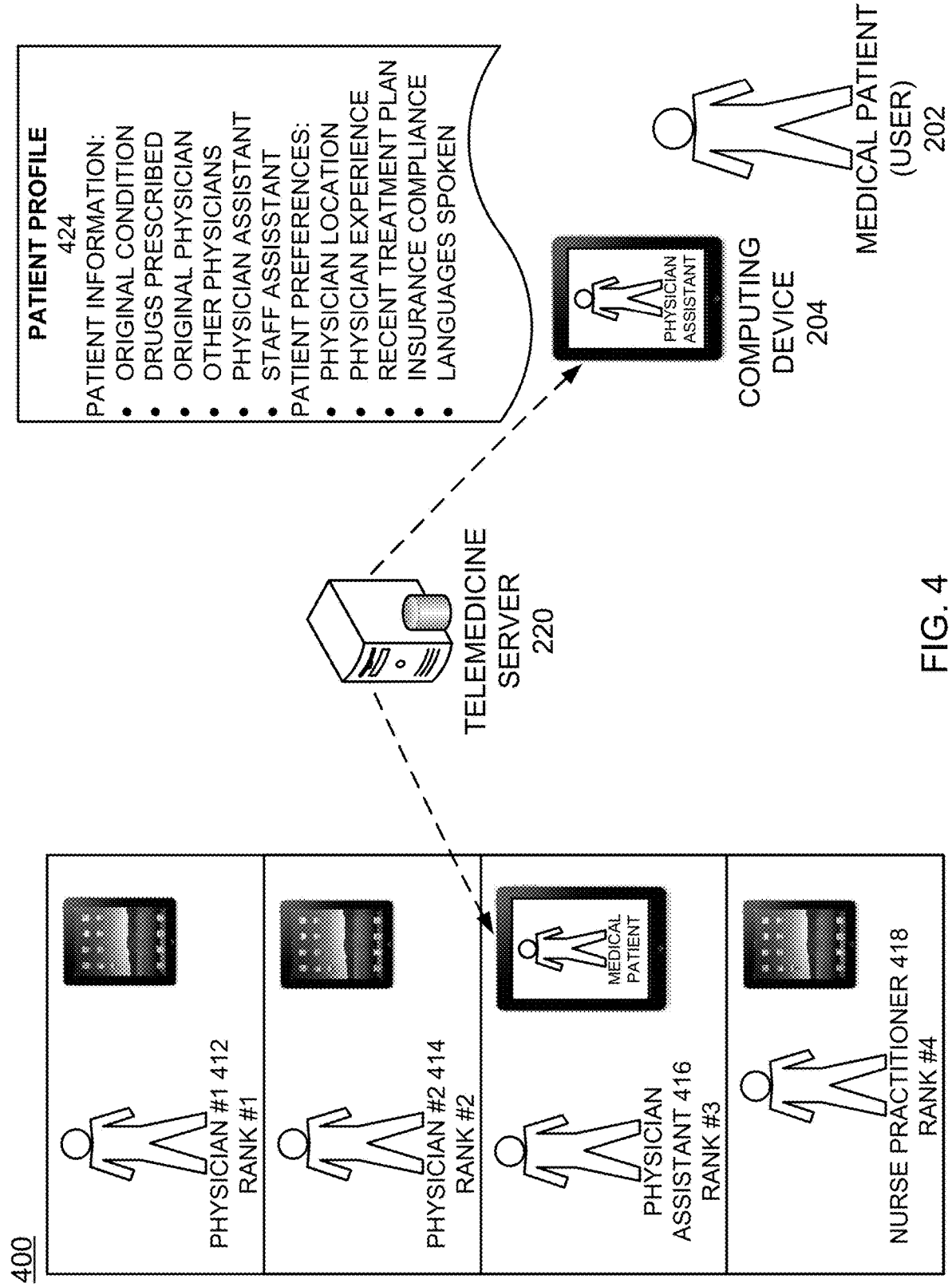
FIG. 4 illustrates a medical professional list presentation and selection operation according to example embodiments of the present application.

FIG. 4 illustrates a medical professional list presentation and selection operation according to example embodiments of the present application. Referring to FIG. 4, the telemedicine server 220 may provide a link that populates a user interface of the user device 204 with a list of ranked physicians 412 and 414 and/or other medical professionals 416 and 418 which can be selected by the patient for an upcoming session. The patient may see the physician and although the rankings were conducted for patient convenience based on the user preferences, the user may see that a female professional is in the list as third option and that other information, such as the physician assistant 416 speaks fluent Hindi and that patient may desire such a professional based on those other options presented to the user computing device 204. In this example, the user has selected physician assistant 416 to participate in an upcoming session where the patient 202 and the assistant 416 will have a live session. The patient profile 424 includes patient information that can be shared with the physician assistant and which was used to perform the ranking and user interface option sequence.

Figure 5:
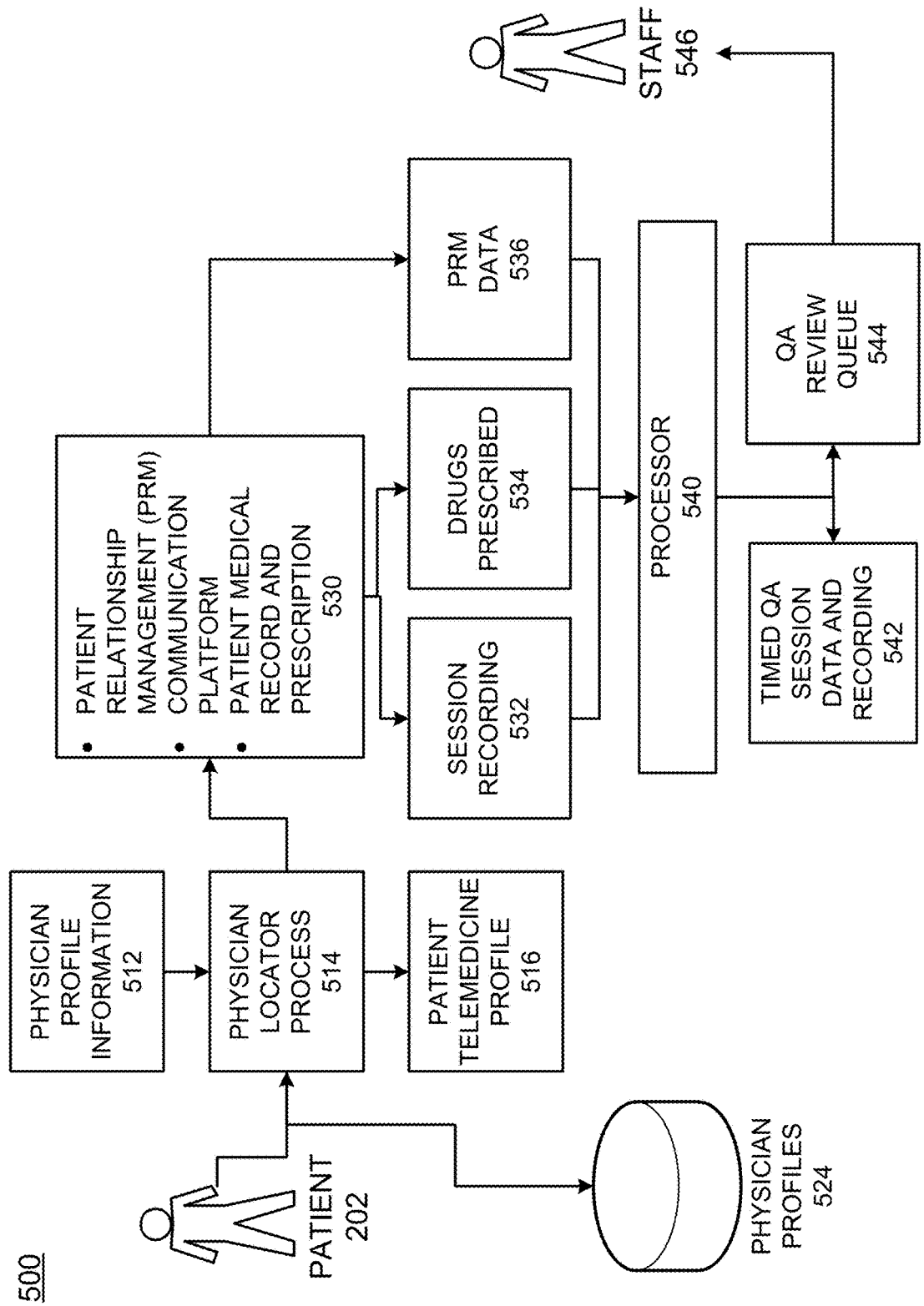
FIG. 5 illustrates a logic flow and data processing example of a telemedicine session according to example embodiments of the present application.

FIG. 5 illustrates a logic flow and data processing example of a telemedicine session according to example embodiments of the present application. Referring to FIG. 5, the logic diagram 500 includes actions taken during and after a live session to ensure patient compliance and correct follow-up procedures. For instance, the patient 202 may initiate the patient locator process 514 which references physician and medical assistant profile information 512 to offer a suggested course of action by the patient, such as establishing a live session based on physician profiles 524 and the corresponding profiles 516 of those professionals within the telemedicine planning process. A processing platform 530 of the telemedicine server 220 may establish a communication platform, a patient relationship management (PRM) procedure and/or a patient medical record and prescription procedure.

In operation, after a session has been completed and the recording has been stored, 532 the patient profile may remain active via a status indicator in the patient profile record stored in the server 220. The parsing of the record may indicate that the medical professional stated "I will prescribe 'drug 1', 'drug 2' and those drugs require a one week and three week follow-up appointment." A parsing engine may identify the follow-up and drug prescription indicators and initiate actions, such as notify pharmacy partner server of drug prescriptions and create calendar entry for additional appointments. Such PRM data 536 may be received and stored for subsequent processing 540 and related actions managed by a quality assurance (QA) quality review module 544 which maintains the actions until the patient profile is deemed satisfied and may be labeled "inactive" until further notice. Current drugs prescribed 534 may also be a factor in identifying a patient profile. The results of the processing may initiate the review queue 544 and may store a data recording 542. A staff member 546 may be assigned to the "active" profile to review the session, outcome and patient condition and may also communicate with the patient until all actions and subsequent actions have been completed.

Figure 6:
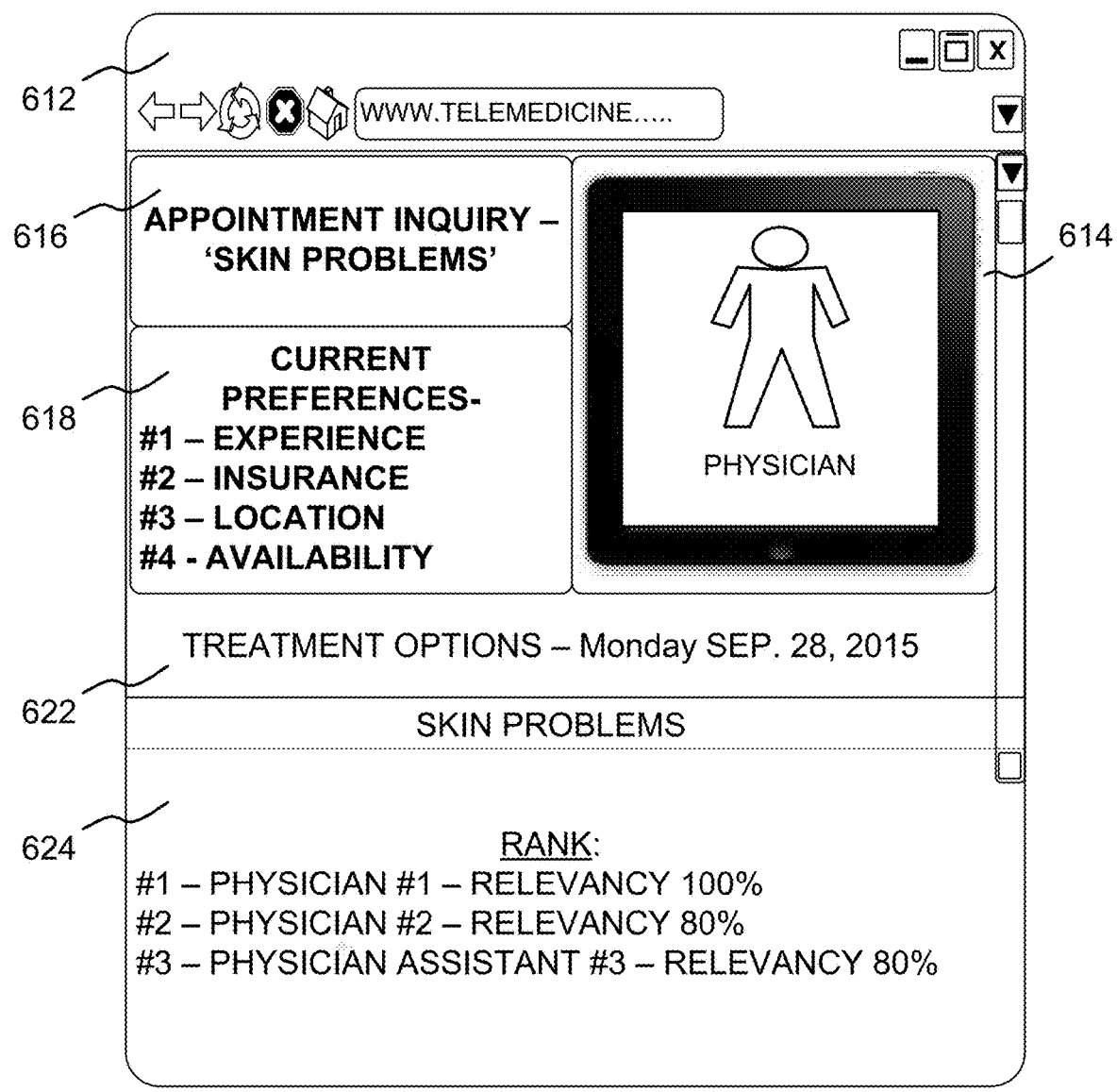
FIG. 6 illustrates a medical patient user interface during a telemedicine communication setup session according to example embodiments of the present application.

FIG. 6 illustrates a medical patient user interface during a telemedicine communication setup session according to example embodiments of the present application. Referring to FIG. 6, the example interface 600 includes the user accessing his or her computing device 204 to launch a web-based browser interface 612 that connects to the telemedicine server 220. The session may include a view of the selected medical professional or physician 614, a focus for the session 616, a current list of the user preferences in order 618, a summary of the appointment 622 and date and the list of medical professionals 624 provided as suggested by the automated creation procedure.

Figure 7:
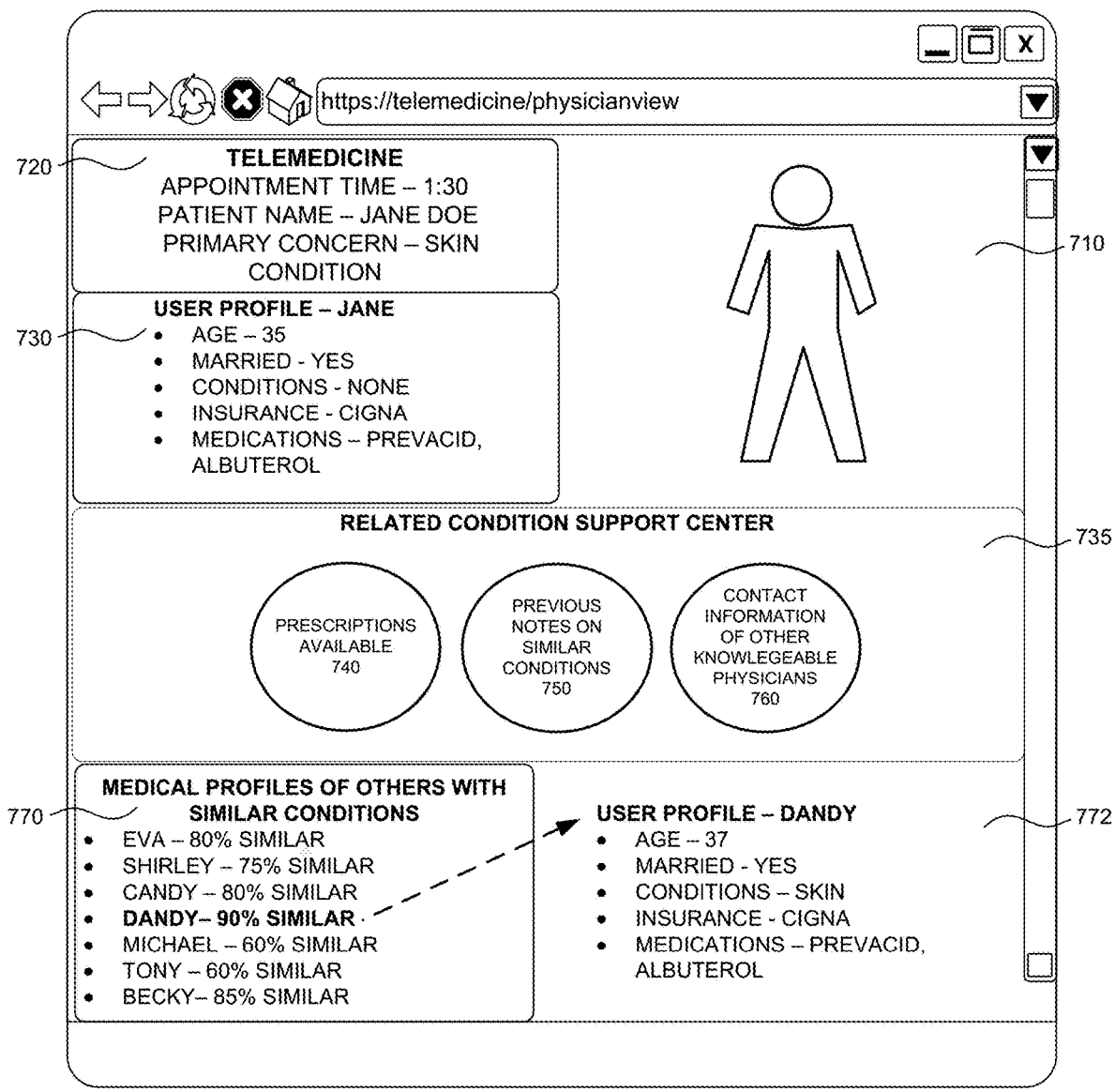
FIG. 7 illustrates a medical assistant user interface during a live telemedicine communication session according to example embodiments of the present application.

FIG. 7 illustrates a medical assistant user interface during a live telemedicine communication session according to example embodiments of the present application. Referring to FIG. 7, the physician view of the live session may include more abundant information to assist the physician or medial professional with caring for the patient. For instance, the web browser interface 700 includes various modules which are automatically populated by information sources pertinent to the session. Initially, a live feed or image data 710 of the patient may be automatically placed in a portion of the portal so the physician can maintain a live network feed of the user and observe the user's present condition. The first segment 720 includes a list of basic session information, such as the appointment time, the patient name, and the purpose of the session. The next segment 730 includes additional details of the patient which may be customized by the physician to have a snapshot of the various details of the patient which are considered useful for the physician during the session. The related condition support center 735 includes various selection options which are populated based on other treatment sessions of the physician or other physicians, the information may be provided blindly without providing patient names to assist with the types of prescriptions 740 that were prescribed for similar skin conditions, notes about the session conclusions 750 and contact information of other physicians 760 for more information retrieval options. The bottom feed or information module 770 may provide a list of patients and a similarity rating that is performed to compare the present patient to the past patients. This provides a simple and effective way for the physician to select and view a similar patient with similar conditions so known treatment options, insurance and profile information 772 can be compared and provided for a quick diagnosis.

Figure 8:
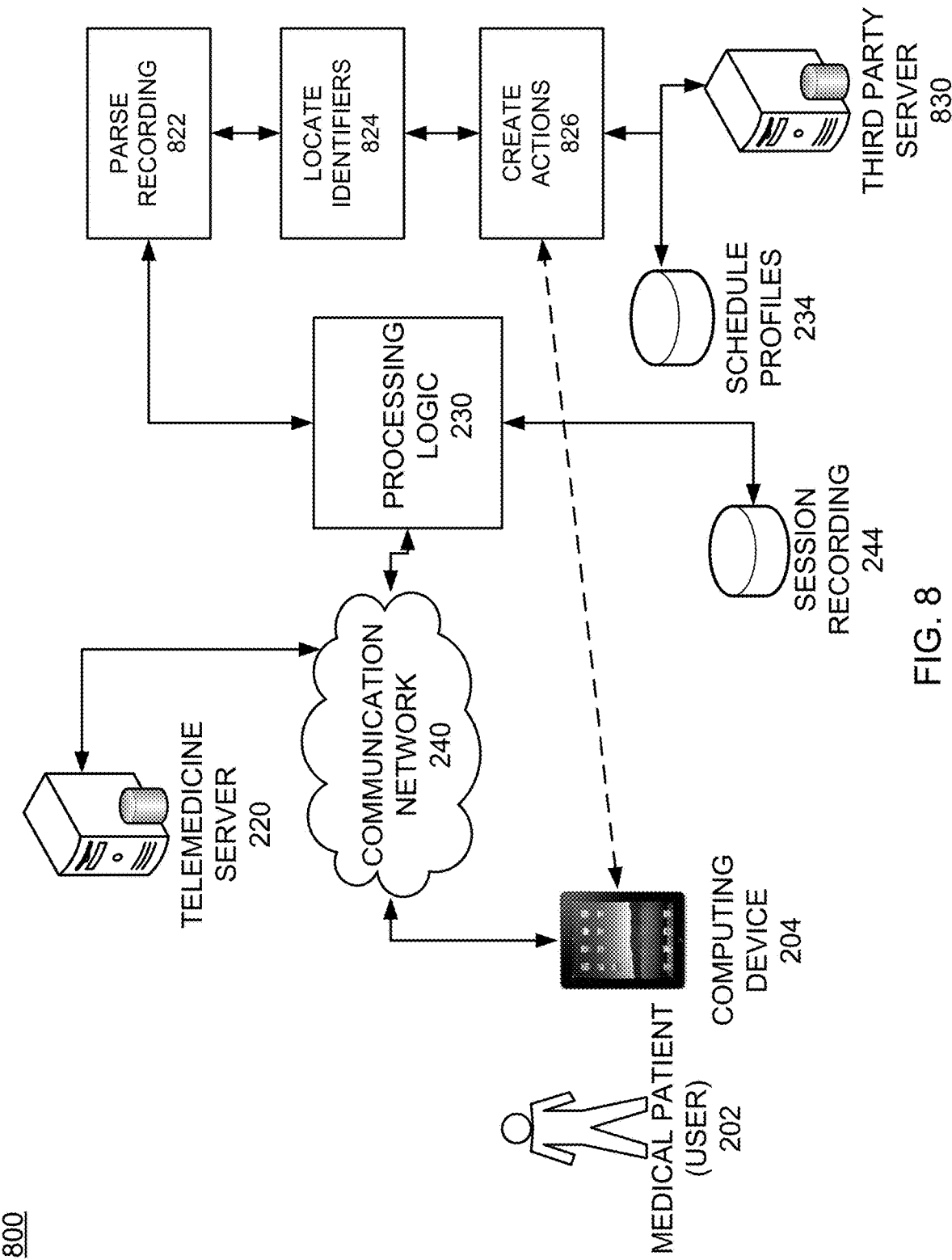
FIG. 8 illustrates a post-telemedicine logic data processing scenario according to example embodiments of the present application.

FIG. 8 illustrates a post-telemedicine logic data processing scenario according to example embodiments of the present application. Referring to FIG. 8, the operations performed after a session 800 has been completed includes at least storing all session data in session recording datastore 244. The recorded data may include audio, video, indicators (prescriptions, follow-up instructions, etc.) and other data that can be easily processed, parsed 822 and used to create actions 826 automatically by a server 220 based on the identified indicators 824. The actions created may include retrieving calendar and schedule information for subsequent follow-up consultations, prescriptions assigned to a third party 830, actions assigned to a third party, performance review, etc.

Figure 9A:
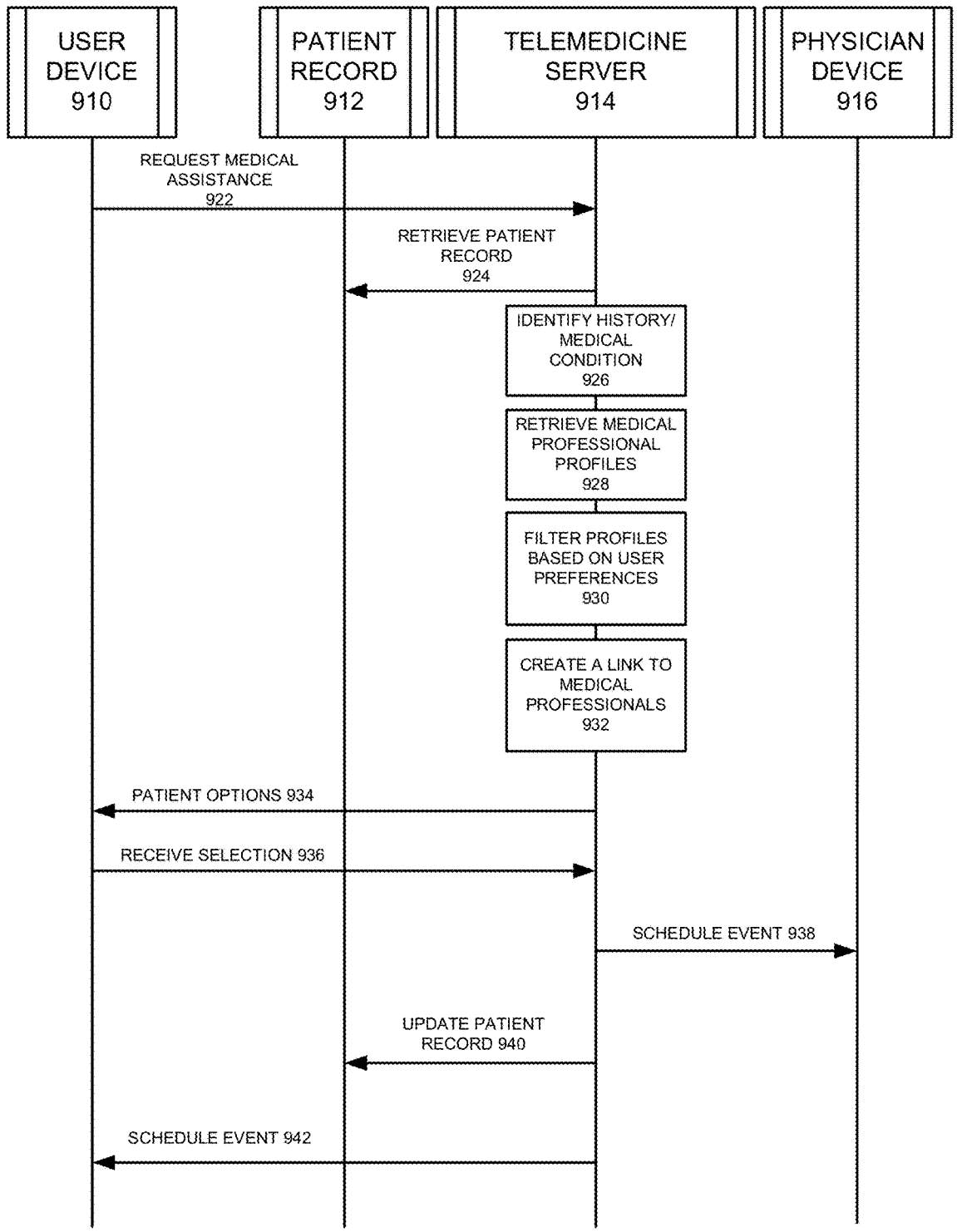
FIG. 9A illustrates a system signaling diagram for a telemedicine setup procedure according to example embodiments of the present application.

FIG. 9A illustrates a system signaling diagram for a telemedicine setup procedure according to example embodiments of the present application. Referring to FIG. 9A, the procedure for establishing a live telemedicine session 900 may include a user device 910 being used by a user/patient to contact the telemedicine service operated by a server 914. A patient record 912 may be referenced for patient information necessary to create and follow-up with a live medical session. In one example method of operation a request for medical assistance 922 is received from a user device 910. After receiving the request, the server 914 retrieves the patient record 924 and determines if the information included in the record is complete. The information may include profile information, current condition information, current medical treatment and prescription information, etc. The medical condition and patient history information is processed to identify the present medical condition 926 and a likely course of treatment beginning with a live telemedicine session with a qualified medical professional 928. The user preferences of the user profile are then applied to limit the list of medical professionals available for the patient via a filtering operation 930. The server 914 will then create a link that populates a user interface with a limited number of results of medical professionals 932 that the patient may select for a live telemedicine session.

The current patient condition status may also be used by scoring in a weighted function the present condition of the patient (i.e., current degree of severity (1-10)), the patient history (i.e., past degree of severity (1-10)), which may be based on age, previous conditions, current health status, previous medications taken, etc. The weighted function may be used as a raw score that can be compared to a decision threshold as to the type of treatment the patient should receive.

The patients options are presented to the patient in the link 934 and the patient may access the link, observe various user profiles and select one or more medical professionals for a live session 936. The application may automatically select the medical professional for the user assuming the user preferences are setup for an automated selection operation. The patient schedule and medical professional schedules are then referenced for availability of appointment times. The patient record 940 and a master schedule 938 are updated to reflect the upcoming appointment in a scheduled event 942 which is then forwarded to the user device for a calendar update and notification to the patient.

In another example, an initial list of medical assistant selections can be provided to the user device. The initial list can be modified and re-forwarded based on specific user input, such as physician requirements or money saving options, etc. Some of the user preferences may include insurance preferences, location preferences, physician experience preferences, existing medical conditions, physician ranking preferences. The procedure of retrieving a plurality of medical professional profiles associated with the medical condition provided by the user may also include identifying the plurality of medical professional profiles that include at least one relevant factor identified by at least one of the plurality of user preferences. The relevant factor may be a comparison of a user preference to a medical professional attribute stored in a medical professional databank. The number of matches between user preferences and physician attributes can initiate creating a relevancy score percentage(s) based on a number of relevant matches corresponding to the user preferences each medical professional profile satisfies. Those relevancy scores can initiate the list creation with the most relevant physician first and the next most relevant after, continuing onward for all relevant results presented.

In one example, sorting and listing criteria may include requiring at least one specialist physician profile, at least one medical assistant and at least one generalist physician profile in the link. In one example, the user profile may be regarded as an incomplete profile, in this case, a request for user medical information is transmitted to the user device and updated user information may then be received so the user profile can be updated to a complete profile. When a patient profile is identified and a live session creation procedure is initiated, an 'active' status for the patient profile is enacted responsive to receiving the request for medical attention. The active status is maintained during the session setup and during the subsequent action performing operations, until the actions have been fulfilled. The inactive status may be reinstated once the appointment has finished assuming there are no subsequent actions to fulfill. When scheduling the live session, medical professional profile schedules are retrieved along with a user schedule for the user device/patient. Appointment times available for the user schedule and the medical professional profile schedules are then observed and included in the appointment times in the link for user selection or an automated script may select an appointment pending user approval.

Figure 9B:
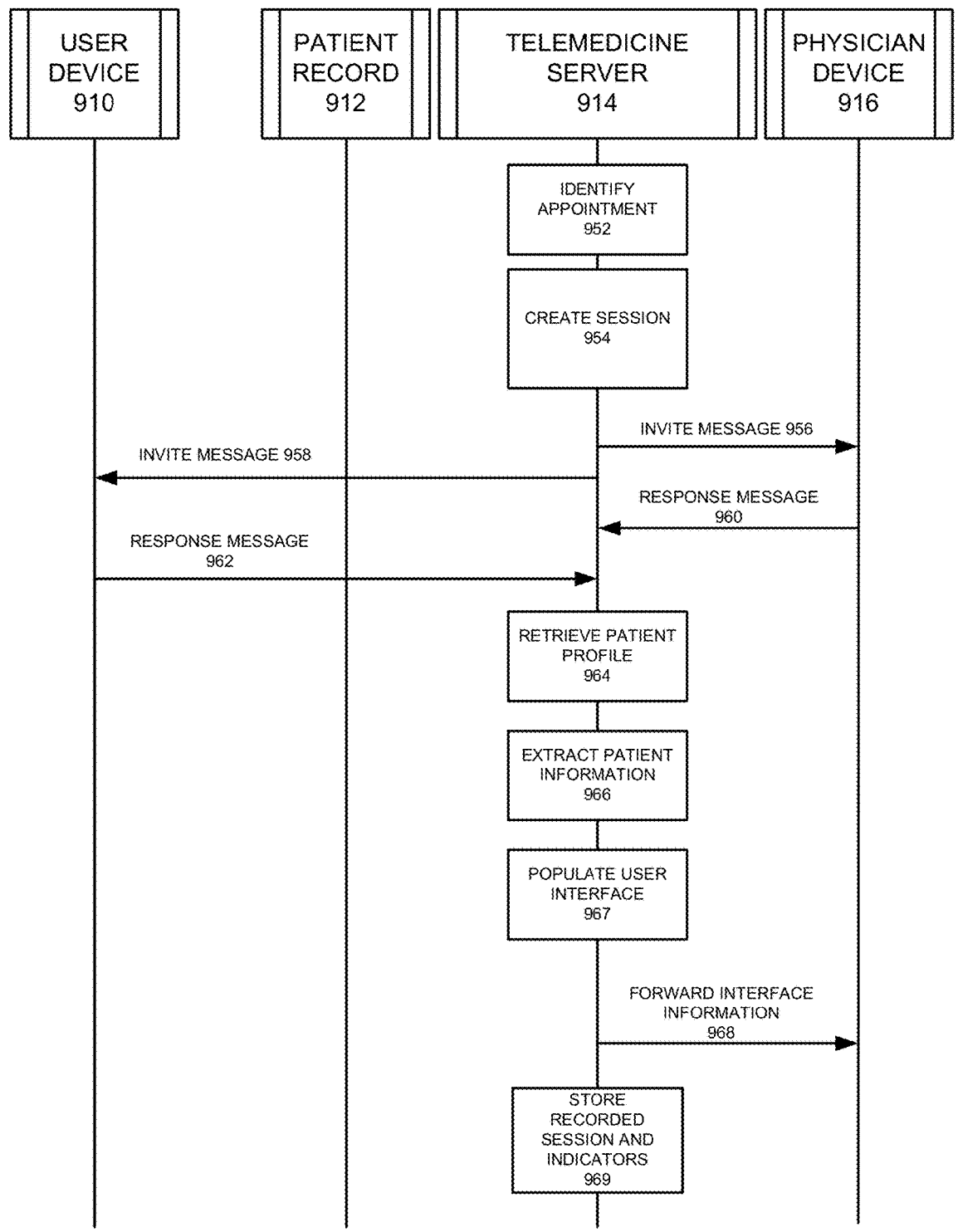
FIG. 9B illustrates a system signaling diagram for a telemedicine execution procedure according to example embodiments of the present application.

FIG. 9B illustrates a system signaling diagram for a telemedicine execution procedure according to example embodiments of the present application. Referring to FIG. 9B, this example pertains to the actual setup of the live communication session. Initially, an upcoming appointment time is identified 952 for a live medical treatment session which is stored in a master calendar entry. The session may then be created 954 and hosted by the server 914. Once the session is setup, a first invitation message 956 is transmitted to a medical professional device associated with a medical professional identified in the calendar entry. Also, a second invitation message 958 is created and sent to a user device associated with a patient identified in the calendar entry, and responsive to receiving a response message from the medical professional device 960 and a response 962 from the user device, a patient profile record associated with the patient is retrieved 964 and a user interface of the medical professional device is populated 967 with extracted patient history information 966 stored in the patient profile record. The medical professional interface of the physician device 916 can then be updated with the relevant information 968. The session information may be updated and stored with relevant indicators 969.

According to another example, at the beginning of the session, vital sign information of the patient can be taken and received and stored from a peripheral sensor attached to the user device, such as pulse, blood pressure and other vital sign information which can be received via BLUETOOTH or via a direct connection such as USB. The vital sign information received may be compared automatically to vital sign information thresholds to identify if an acceptable threshold value exists and whether an elevated health concern exists. The user interface of the medical professional device can then be populated with the vital sign information and an indication regarding whether the elevated health concern exists.

The session may also provide identifying a present health condition associated with the user and retrieving previous treatment information associated with the present health condition comprising at least one prescribed drug, and populating a portion of the medical professional user interface with the previous treatment information and the at least one prescribed drug. Also, the previous treatment information associated with the present health condition can also be retrieved from a patient plan associated with a previously treated patient. Another portion of the medical professional user interface can be populated with other treatment options associated with the present health condition. The audio and the video created during the live medical treatment session can be created with inserted indicators that were made during the live medical treatment session. The indicators may be unrefined and may require parsing prior to the indicators being set and embedded into recording files. The indicators may be flags that are readily recognized by the application processor. For example, when a parsed word or interest is identified, the parse result (i.e., medication—XYZ topical skin cream) may be identified and placed at the portion of the recording where the physician stated the need for such a prescription. The recording may be re-stored in the file with the indicators for future reference. The indicators may represent various different subsequent treatment options for the patient.

Figure 9C:
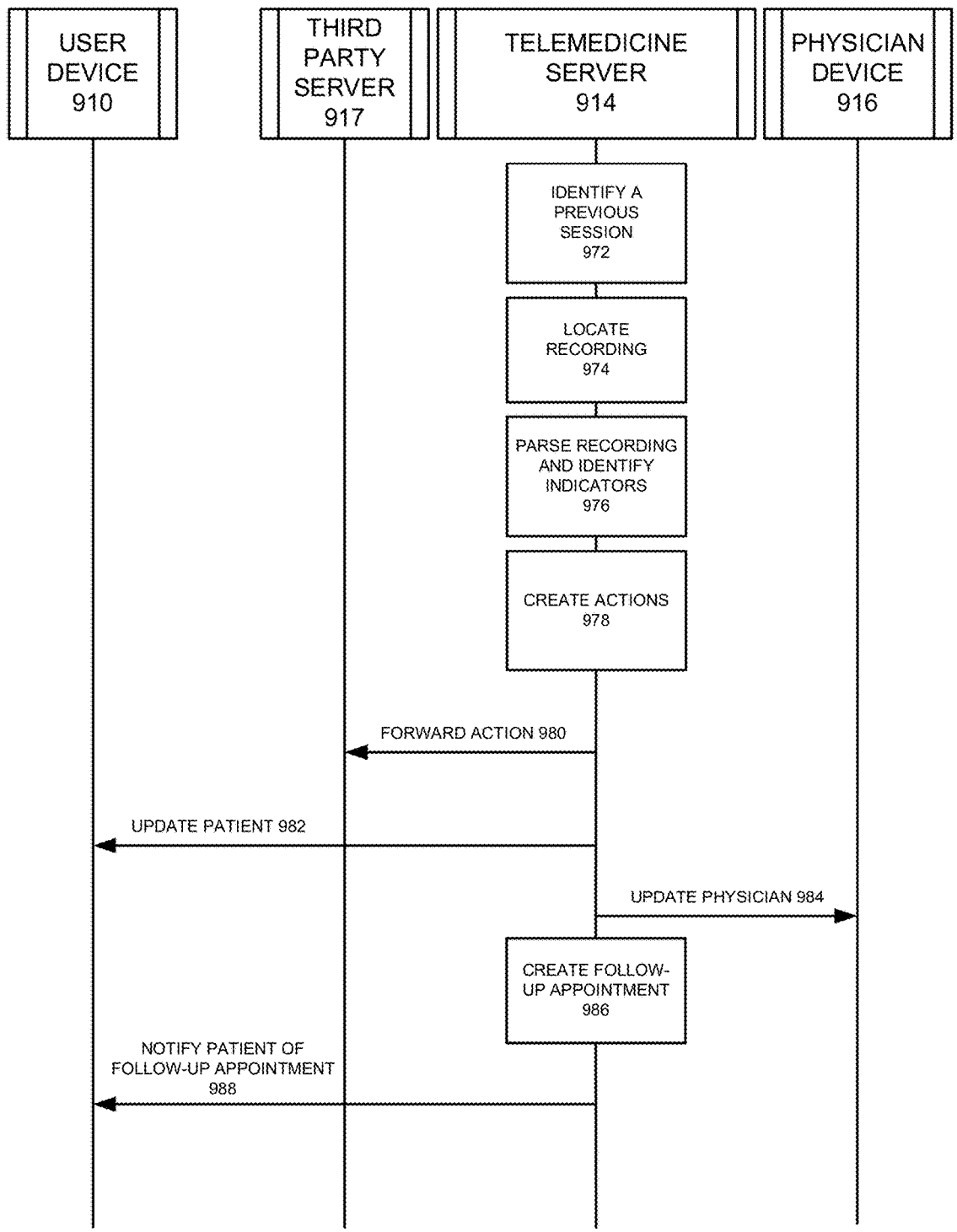
FIG. 9C illustrates a system signaling diagram for a telemedicine follow-up procedure according to example embodiments of the present application.

FIG. 9C illustrates a system signaling diagram for a telemedicine follow-up procedure according to example embodiments of the present application. Referring to FIG. 9C, the live medical treatment session record may be identified 972 after a session is completed 972. The recording can then be located 973 and parsed 976 to identify any word or terms which invoke indicators that are then created and used to create subsequent actions 978. Those actions may be used to forward messages 980 to various third parties 917 for other actions to be performed for the medical patient based on the indicator. Any time an action is completed that requires patient knowledge, the patient may be updated 982 as well as the physician 984. The at least one subsequent action may include at least one of a prescription fulfillment action, a follow-up consultation action, a laboratory workup action, and an ongoing monitoring vital sign action. For example, a prescription indicator stored in the recording can be located and at least one prescription prescribed by the medical professional can be extracted. A follow-up appointment indicator may be identified and the calendar can be retrieved to create a follow-up appointment 986. The physician may require a follow-up with a specialist (i.e., Dermatologist) and the parser may identify follow-up and Dermatologist in the same sentence and recognize the need to retrieve a medical professional profile for such a physician and a calendar for appointment times each of which are part of the same action. The patient device 910 may also be updated 988 of any upcoming appointments.

In the example of a prescription action, the action to fill a prescription may include communicating a message with a pharmacy computing device and/or assigning the medical patient to another medical professional. Any time actions are created, a staff medical assistant may be notified and assigned the pending active status of a patient until all actions are performed. This enables the patient to communicate with the staff member so the questions and concerns can be addressed between physician appointments.

Figure 10:
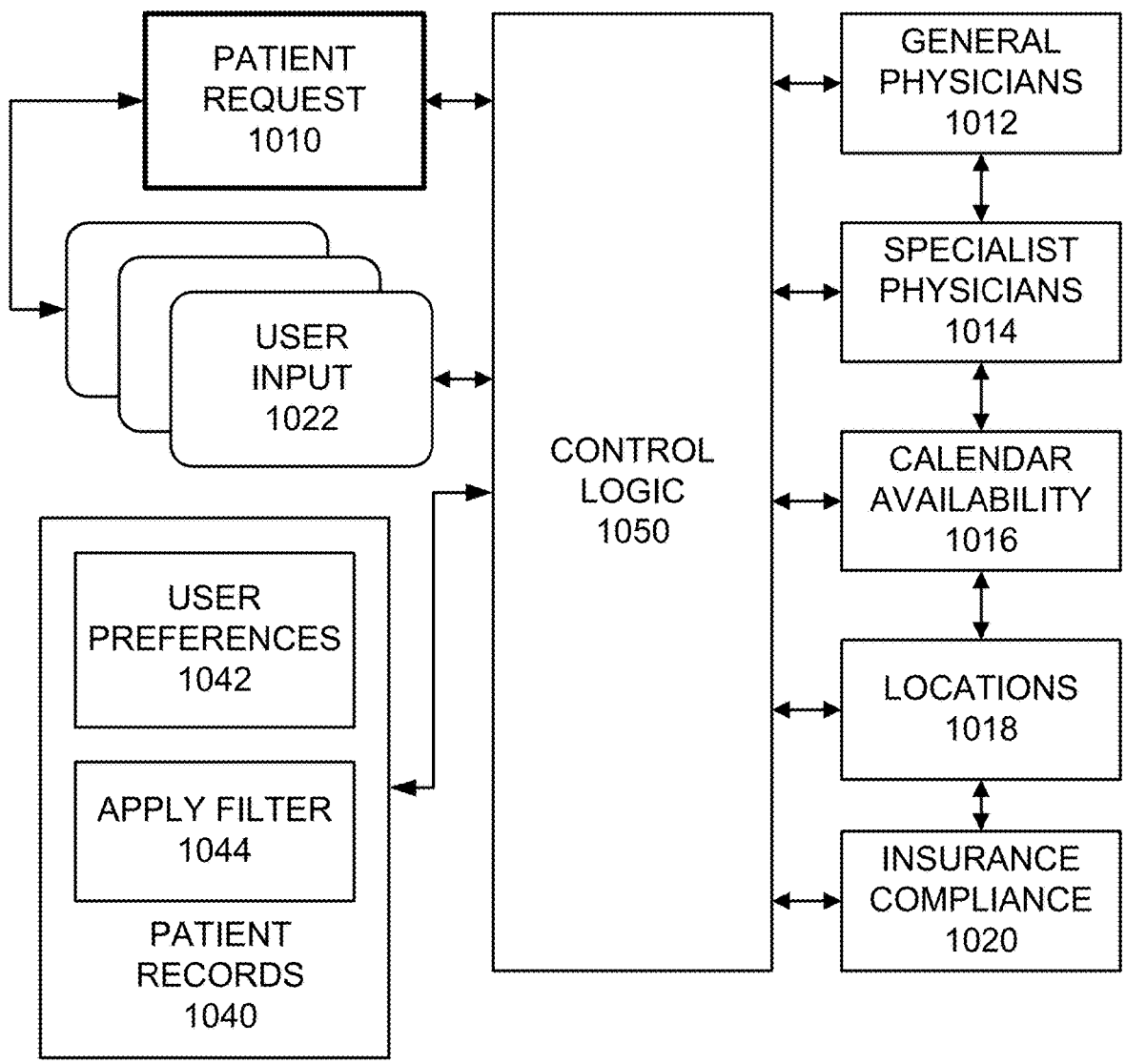
FIG. 10 illustrates a logic processing diagram according to example embodiments of the present application

FIG. 10 illustrates a logic processing diagram according to example embodiments of the present application. Referring to FIG. 10, the logic configuration 1000 includes a control logic 1050 which may be a processor or other processing entity capable of receiving input and processing the input data to create output. In this logic example, the patient request 1010 triggers action by the processor 1050 based on other user input parameters 1022 and user preferences 1042 which can invoke a filter 1044 to be used to process telemedicine appointment scheduling based on general physician suggestions 1012, specialist physician suggestions 1014, calendar availability 1016, locations of the patient and/or the physician facilities 1018 and insurance compliance 1020.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example FIG. 11 illustrates an example network element 1100, which may represent any of the above-described network components of the other figures.

Figure 11:
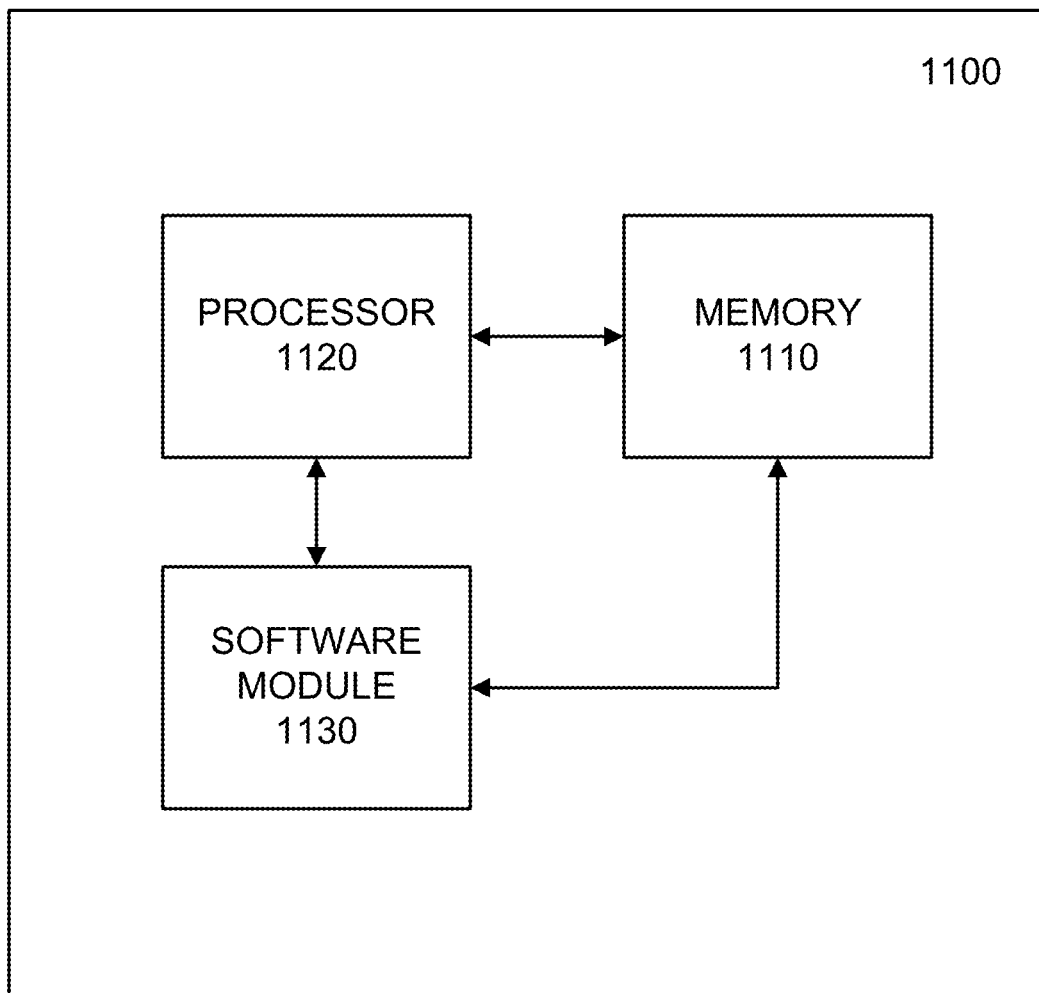
FIG. 11 illustrates an example network entity device configured to store instructions, software, and corresponding hardware for executing the same, according to example embodiments of the present application.

As illustrated in FIG. 11, a memory 1110 and a processor 1120 may be discrete components of the network entity 1100 that are used to execute an application or set of operations. The application may be coded in software in a computer language understood by the processor 1120, and stored in a computer readable medium, such as, the memory 1110. The computer readable medium may be a non-transitory computer readable medium that includes tangible hardware components in addition to software stored in memory. Furthermore, a software module 1130 may be another discrete entity that is part of the network entity 1100, and which contains software instructions that may be executed by the processor 1120. In addition to the above noted components of the network entity 1100, the network entity 1100 may also have a transmitter and receiver pair configured to receive and transmit communication signals (not shown).

Although an exemplary embodiment of the system, method, and computer readable medium of the present application has been illustrated in the accompanied drawings and described in the foregoing detailed description, it will be understood that the application is not limited to the embodiments disclosed, but is capable of numerous rearrangements, modifications, and substitutions without departing from the spirit or scope of the application as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments of the present application. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the application as discussed above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent, while remaining within the spirit and scope of the application. In order to determine the metes and bounds of the application, therefore, reference should be made to the appended claims.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method comprising:
    accessing a calendar application and identifying a calendar entry of an upcoming appointment time for a live medical treatment session between a patient and a medical professional;
    creating a communication session hosted by a server;
    transmitting a first invitation message to a medical professional device based on an identifier of the medical professional identified in the calendar entry;
    transmitting a second invitation message to a user device based on an identifier of the patient identified in the calendar entry;
    responsive to receiving a response message from the medical professional device, retrieving a patient profile record associated with the patient, generating a live image feed of the patient, and automatically populating the live image feed within a first portion of a medical professional user interface displayed on the medical professional device and automatically populating a second portion of the medical professional user interface with patient history information stored in the patient profile record, wherein the medical professional user interface is automatically updated with relevant information and stored with relevant indicators;
    identifying a present health condition associated with the user; and populating a third portion of the medical professional user interface with a list of one or more other patients with at least a similar health condition of the user and at least one of a similarity rating or a method of treatment or prescription used for the one or more other patients.

2. The method of claim 1, further comprising:
receiving vital sign information of the patient from a peripheral sensor attached to the user device;
processing the vital sign information and comparing the vital sign information to an acceptable threshold value to identify whether an elevated health concern exists; and
populating the user interface of the medical professional device with the vital sign information and an indication regarding whether the elevated health concern exists.

3. The method of claim 1, further comprising:
retrieving previous treatment information associated with the present health condition, the previous treatment information comprising at least one prescribed drug; and
populating the second portion of a medical professional user interface with the previous treatment information and the at least one prescribed drug.

4. The method of claim 3, wherein the previous treatment information associated with the present health condition is retrieved from a patient plan associated with a previously treated patient.

5. The method of claim 1, further comprising:
populating the third portion of the medical professional user interface with other treatment options associated with the present health condition.

6. The method of claim 1, further comprising:
recording audio and video created during the live telemedicine session;
creating indicators during the live telemedicine session and embedding the indicators into a file associated with the recorded audio and video; and
storing the file with the recorded audio and video and the indicators.

7. The method of claim 6, wherein the indicators represent subsequent treatment options for the patient.

8. An apparatus comprising:
a processor configured to
access a calendar application and identify a calendar entry of an upcoming appointment time for a live medical treatment session between a patient and a medical professional;
create a communication session hosted by a server; and
transmit a first invitation message to a medical professional device associated with the medical professional based on an identifier of the medical professional identified in the calendar entry and transmit a second invitation message to a user device based on an identifier of the patient identified in the calendar entry, and
responsive to receiving a response message from the medical professional device, retrieve a patient profile record associated with the patient, generate a live image feed of the patient, and automatically populate the live image feed within a first portion of a medical professional user interface displayed on the medical professional device and automatically populate a second portion of the medical professional user interface with patient history information stored in the patient profile record, wherein the medical professional user interface is automatically updated with relevant information and stored with relevant indicators;
identify a present health condition associated with the user; and
populate a third portion of the medical professional user interface with a list of one or more other patients with at least a similar health condition of the user and at least one of a similarity rating or a method of treatment or prescription used for the one or more other patients.

9. The apparatus of claim 8, further comprising:
a receiver configured to receive vital sign information of the patient from a peripheral sensor attached to the user device,
wherein the processor is further configured to process the vital sign information and compare the vital sign information to an acceptable threshold value to identify whether an elevated health concern exists, and
populate the user interface of the medical professional device with the vital sign information and an indication regarding whether the elevated health concern exists.

10. The apparatus of claim 8, wherein the processor is further configured to retrieve previous treatment information associated with the present health condition, the previous treatment information comprising at least one prescribed drug, and populate the second portion of the medical professional user interface with the previous treatment information and the at least one prescribed drug.

11. The apparatus of claim 10, wherein the previous treatment information associated with the present health condition is retrieved from a patient plan associated with a previously treated patient.

12. The apparatus of claim 8, wherein the processor is further configured to populate the third portion of the medical professional user interface with other treatment options associated with the present health condition.

13. The apparatus of claim 8, wherein the processor is further configured to record and video created during the live telemedicine session, create indicators during the live telemedicine session, embed the indicators into a file associated with the recorded audio and video, and store a file with the recorded audio and video and the indicators.

14. The apparatus of claim 13, wherein the indicators represent subsequent treatment options for the patient.

15. A non-transitory computer readable storage medium configured to store instructions that when executed cause a processor to perform:
accessing a calendar application and identifying a calendar entry of an upcoming appointment time for a live medical treatment session between a patient and a medical professional;
creating a communication session hosted by a server;
transmitting a first invitation message to a medical professional device based on an identifier of the medical professional identified in the calendar entry;
transmitting a second invitation message to a user device based on an identifier of the patient identified in the calendar entry;
responsive to receiving a response message from the medical professional device, retrieving a patient profile record associated with the patient, generating a live image feed of the patient, and automatically populating the live image feed within a first portion of a medical professional user interface displayed on the medical professional device and automatically populating a second portion of the medical professional user interface with patient history information stored in the patient profile record, wherein the medical professional user interface is automatically updated with relevant information and stored with relevant indicators;

identifying a present health condition associated with the user; and populating a third portion of the medical professional user interface with a list of one or more other patients with at least a similar health condition of the user and at least one of a similarity rating or a method of treatment or prescription used for the one or more other patients.

16. The non-transitory computer readable storage medium of claim 15, wherein the processor is further configured to perform:

receiving vital sign information of the patient from a peripheral sensor attached to the user device;

processing the vital sign information and comparing the vital sign information to an acceptable threshold value to identify whether an elevated health concern exists; and populating the user interface of the medical professional device with the vital sign information and an indication regarding whether the elevated health concern exists.

17. The non-transitory computer readable storage medium of claim 15, wherein the processor is further configured to perform:

retrieving previous treatment information associated with the present health condition, the previous treatment information comprising at least one prescribed drug; and populating the second portion of the medical professional user interface with the previous treatment information and the at least one prescribed drug.

18. The non-transitory computer readable storage medium of claim 17, wherein the previous treatment information associated with the present health condition is retrieved from a patient plan associated with a previously treated patient.

19. The non-transitory computer readable storage medium of claim 15, wherein the processor is further configured to perform populating the third portion of the medical professional user interface with other treatment options associated with the present health condition.

20. The non-transitory computer readable storage medium of claim 15, wherein the processor is further configured to perform:

recording audio and video created during the live telemedicine session;

creating indicators during the live telemedicine session and embedding the indicators into a file associated with the recorded audio and video; and storing the file with the audio and video and the indicators.

* * * * *